United States Patent
Zhang et al.

(10) Patent No.: US 12,050,168 B2
(45) Date of Patent: Jul. 30, 2024

(54) METHOD FOR DETERMINING A MATRIX PERMEABILITY OF A SUBSURFACE FORMATION

(71) Applicant: ARAMCO SERVICES COMPANY, Houston, TX (US)

(72) Inventors: Jilin Jay Zhang, Houston, TX (US); Hui-Hai Liu, Katy, TX (US); Jewel Duncan, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 269 days.

(21) Appl. No.: 17/729,485

(22) Filed: Apr. 26, 2022

(65) Prior Publication Data

US 2023/0341312 A1     Oct. 26, 2023

(51) Int. Cl.
*G01N 15/08* (2006.01)
*G01N 7/10* (2006.01)
*G01N 33/24* (2006.01)

(52) U.S. Cl.
CPC .......... *G01N 15/0826* (2013.01); *G01N 7/10* (2013.01); *G01N 15/0806* (2013.01); *G01N 33/24* (2013.01)

(58) Field of Classification Search
CPC .... G01N 15/00; G01N 15/08; G01N 15/0806; G01N 15/26; G01N 7/00; G01N 7/10; G01N 33/24
See application file for complete search history.

(56) References Cited

U.S. PATENT DOCUMENTS

| | | | |
|---|---|---|---|
| 9,335,245 B2 | 5/2016 | Song et al. | |
| 10,677,707 B2 | 6/2020 | Dusterhoft et al. | |
| 2016/0334322 A1* | 11/2016 | Ramakrishnan | ... G01N 15/0826 |
| 2020/0386664 A1 | 12/2020 | Zhang et al. | |
| 2022/0056798 A1* | 2/2022 | Zhang | ............ E21B 47/117 |

FOREIGN PATENT DOCUMENTS

CN        107014731 B     6/2019

OTHER PUBLICATIONS

Chen, Huangye et al., "A method for correcting low permeability laboratory measurements for leaks: Theory, methodology and algorithms"; Journal of Natural Gas Science and Engineering; vol. 56; pp. 608-618; Aug. 2018 (11 pages).

Gan, Zheng et al., "Fast Pressure-Decay Core Permeability Measurement for Tight Rocks"; Petrophysics; vol. 59, Issue 5, Paper No. SPWLA-2018-v59n5a3; pp. 606-616; Oct. 2018 (11 pages).

Zhang, Jilin Jay et al., "Matrix permeability measurement from fractured unconventional source-rock samples: Method and application"; Journal of Contaminant Hydrology; vol. 233, Article: 103663; pp. 1-6; Aug. 2020 (6 pages).

* cited by examiner

*Primary Examiner* — Nguyen Q. Ha
(74) *Attorney, Agent, or Firm* — Osha Bergman Watanabe & Burton LLP

(57) ABSTRACT

A method for determining a matrix permeability of a subsurface formation, including the steps: acquiring a core from the subsurface formation, imposing a fluid to the core until the core is saturated with the fluid, conducting a pressure-pulse decay (PD) method on an upstream and a downstream side of the core by applying a pressure-pulse on the upstream and the downstream side of the core, and determining the matrix permeability from decays of the pressure-pulses on the upstream side and downstream side, respectively.

20 Claims, 7 Drawing Sheets

METHOD FOR DETERMINING A MATRIX PERMEABILITY OF A SUBSURFACE FORMATION

BACKGROUND

Permeability is related to the fluid conductivity of a material and characterizes the ease with which a fluid can be made to flow through the material by an applied pressure gradient. Fracture permeability is the ease with which fluid flows through natural and/or induced fractures in a shale (unconventional reservoirs such mudrocks). On the other hand, matrix permeability is the ease with which a fluid flows through the intact portion of a shale, i.e., the shale matrix.

Shales and coals may exhibit a matrix permeability of less than 0.001 md, which is called ultra-low matrix permeability. Measuring ultra-low matrix permeability is a challenge for conventional laboratory-based methods. Small diameter core plugs or crushed rock-samples are used to reduce measurement times of the matrix permeability. For core plug analysis, pressure-pulse decay (PDP) or steady-state (SS) methods are commonly employed in laboratories, with the core plug sample subjected to confining stress.

As the values of the matrix permeability from crushed rocks have many limitations, more attention is given to measurements on matrix permeability from core plugs taken from cores. A practical method to measure the values of the matrix permeability from fractured source cores is by the commonly used PD method.

Shale matrix permeability is one of the most important parameters for characterizing a source rock reservoir and for predicting hydrocarbon production. The low matrix permeability and the presence of induced fractures during retrieval of the cores, the transportation of the cores, and during the plugging process (extracting/drilling a core plug from a rock core) make the accurate measurement of the true matrix permeability for source rocks a significant challenge for the oil and gas industry.

The conventional SS method and the PD method on core plugs taken from cores mainly measure the matrix permeability of fractures when present. The Gas Research Institute (GRI) method uses the decay of the pressure-pulse on crushed cores. The GRI method is designed to overcome the difficulty associated with the induced fractures. The measurement results are sensitive to the particle size of the crushed cores and also need correction of the Knudsen diffusion effect. Moreover, the GRI method is limited to the unconfined stress condition.

Accordingly, there exists a need for a method for determining a matrix permeability of a subsurface formation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for determining a matrix permeability of a subsurface formation, comprising the steps: acquiring a core from the subsurface formation, imposing a fluid to the core until the core is saturated with the fluid, conducting a pressure-pulse decay (PD) method on an upstream and a downstream side of the core by applying a pressure-pulse on the upstream and the downstream side of the core, and determining the matrix permeability from decays of the pressure-pulses on the upstream side and downstream side.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying FIGS. Like elements in the various FIGS. are denoted by like reference numerals for consistency.

DETAILED DESCRIPTION

In the following detailed description of embodiments of the disclosure, numerous specific details are set forth to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular order of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element; and the first element may encompass more than one element and succeed (or precede) the second element in an ordering of elements.

In one aspect, embodiments disclosed herein relate to a method for determining a matrix permeability of a subsurface formation. The method involves acquiring a core from the subsurface formation, imposing a fluid to the core until the core is saturated with the fluid, conducting a pressure-pulse decay (PD) method on an upstream and a downstream side of the core by applying a pressure-pulse on the upstream and the downstream side of the core, and determining the matrix permeability from decays of the pressure-pulses on the upstream side and downstream side. The core may be a core sample or a subset of an entire piece of a core, respectively.

Embodiments of the present disclosure may provide at least one of the following advantages. The method for determining a matrix permeability of a subsurface formation allows the measuring of the matrix permeability of partially fractured cores allows determining a matrix permeability of a subsurface formation.

Figure 1:
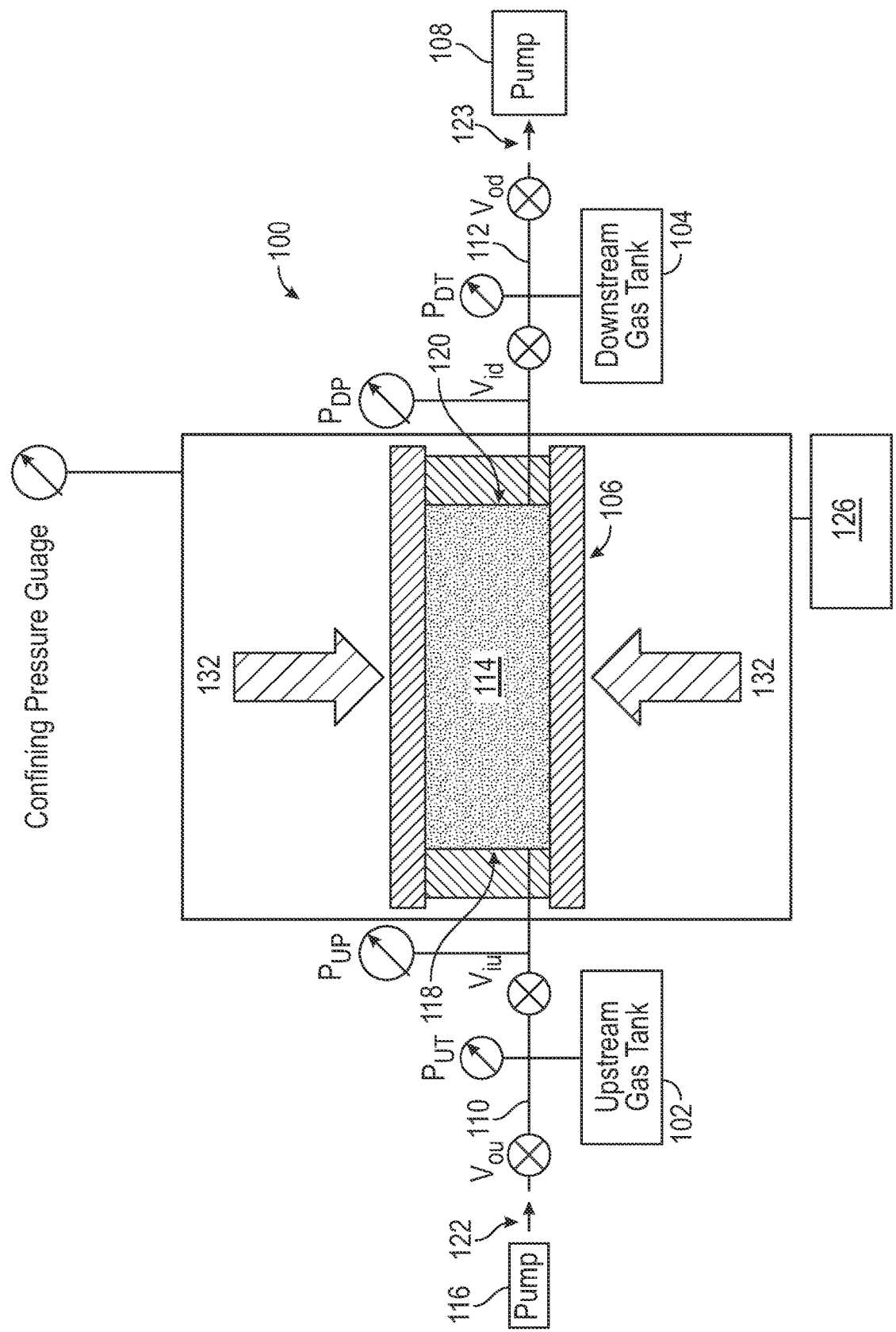
FIG. 1 illustrates a laboratory measurement system 100 for determining fracture permeability and matrix permeability of a subsurface formation, according to one or more embodiments.

FIG. 1 illustrates an experimental laboratory measurement system 100 for determining matrix permeability of a subsurface formation, according to one or more embodiments.

The system 100 includes a core holder 106 (also called sample cell, or pressure cell) configured to hold a core 114. Specifically, a core 114 is disposed in the core holder 106. The core 114 is cylindrical with a length L and includes sleeves around it and lies in the core holder 106 horizontally (as shown in FIG. 1), vertically, or in any orientation. An upstream pipe 110 connects the core holder 106 with a first pump 116, such that the first pump 116 pumps a fluid to a first end face 118 of the core 114. Accordingly, a downstream pipe 112 connects the core holder 106 to a second pump 108, such that the second pump 108 can pump the fluid from a second end face 120 of the core 114. The first and second pumps 116, 108 apply downstream and upstream pore pressures 122, 123 with a pore fluid, which may be a gas or a liquid, to the core 114 within the sleeves. The pressure 132 of a fluid generates a confining pressure 132 to the interior of the core holder 106 and thus to the core 114. The confining pressure 132 is depicted by arrows in FIG. 1. There is no communication between the pore fluid within the sleeves and the confining fluid outside the sleeves within the core holder 106. The upstream and downstream pore pressures 122, 123 may be the same or different, while the confining pressure 132 is always higher than the highest pore pressure (the higher of the upstream and downstream pore pressures 122, 123, in case there is a difference between the upstream and downstream pore pressures 122, 123).

Furthermore, an upstream gas tank 102 is connected to the upstream pipe 110, and a downstream gas tank 104 is connected to the downstream pipe 112. The upstream and downstream gas tanks 102, 104 are filled with a noble gas, such as nitrogen. A first pressure gauge $P_{UT}$ is connected to the upstream gas tank 102 for measuring and recording the pressure of the noble gas in the upstream gas tank 102. A second pressure gauge $P_{DT}$ is connected to the downstream gas tank 104 for measuring and recording the pressure of the noble gas in the downstream gas tank 104. Moreover, the upstream pipe 110 includes an inner upstream valve $V_{iu}$ disposed between the upstream gas tank 102 and the core holder 106, and an outer upstream valve $V_{ou}$ disposed between the upstream gas tank 102 and the first pump 116. Accordingly, the downstream pipe 112 includes an inner downstream valve $V_{id}$ disposed between the core holder 106 and the downstream gas tank 104, and an outer downstream valve $V_{od}$ disposed between the downstream gas tank 104 and the second pump 108.

The confining pressure 132 is monitored and recorded by the confining pressure gauge and maintained by a confining pressure pump 126. The upstream pore pressure 122 is monitored and recorded by an upstream pressure gauge $P_{UP}$ disposed between the inner upstream valve $V_{iu}$ and the core 114, and the downstream pore pressure 123 is monitored and recorded by a downstream pressure gauge $P_{DP}$ disposed between the core 114 and the inner downstream valve $V_{id}$. The upstream pressure gauge $P_{UP}$, downstream pressure gauge $P_{DP}$, first pressure gauge $P_{UT}$ of the upstream gas tank 102, and second pressure gauge $P_{DT}$ of the downstream gas tank 104 can also include temperature transducers.

Pumps (116 and 108 shown in FIG. 1), connected to the upstream and downstream gas tanks 102, 104, measure the temperature, pressure, volume, and mass flow rates to and/or from the core 114. Pressure and temperature transducers monitor the pressure and temperature conditions at different locations during the test. The pressure in the upstream and downstream pipes 110, 112 are controlled from the pumps 116 and 108 on the upstream and downstream side.

The core holder 106 includes flow lines leading from the core 114 to the pumps through a cell wall of the core holder 106. The core holder 106 includes end pieces in a sample assembly that is put into a pressure cell (not shown in FIG. 1), and that converts the pressure into a measurable electrical signal. Within the pressure cell, there is a confining fluid whose pressure is regulated by a confining pump (not shown in FIG. 1). The pressure of the confining fluid is controlled and recorded by a computer program. The pipes (pore lines) 110, 112 and the first and second (pore) pumps 116, 108 are filled with a working fluid, the pressure of which is regulated and recorded by several apparatus. The core 114, the cell/core holder 106 containing the sample assembly, the pumps, and the pore lines 110, 112 are all put into an oven controlled by the computer program, so that the temperature remains stable throughout the experiment. The system 100 is flexible such that both upstream and downstream gas tanks 102, 104 are symmetrical or asymmetrical, with the dead volumes (the volume between inner upstream valve $V_{iu}$ to the first end face 118 of the core and the volume between inner downstream valve $V_{id}$ and the second end face 120 of the core, respectively) being reduced to as small as possible. In one or more embodiments, a single pore pump may be used if the outer ends of pore lines 110, 112 are connected to the same pump.

To conduct a measurement, the confining pressure 132 is raised to a desired level. With all the valves open, a saturation pressure $P_s$ is applied to the pore lines 110, 112 for some time. When the pore fluid reaches equilibrium, all the pore fluid pressure gauges ($P_{UP}$, $P_{DP}$, $P_{UT}$, $P_{DT}$) read the same at a saturation pressure $P_s$. Then the inner valves $V_{iu}$ and $V_{id}$ are closed. The pumps 116 and 108 apply pressure pulses and the reading of the pressure gauges $P_{UT}$, $P_{DT}$ are slightly higher than the saturation pressure $P_s$, as read by the pressure gauges $P_{UP}$, and $P_{DP}$. The pulse heights, i.e., the difference between the pressure gauges $P_{UT}$ and $P_{UP}$, and between the pressure gauges $P_{DT}$ and $P_{DP}$ are preferably the same, and should be a fraction, e.g., 5% or 10% of the saturation pressure $P_s$. Then, the outer valves $V_{ou}$ and $V_{od}$ are closed and the inner valves $V_{iu}$ and $V_{id}$ are open to start the measurement.

Figure 2:
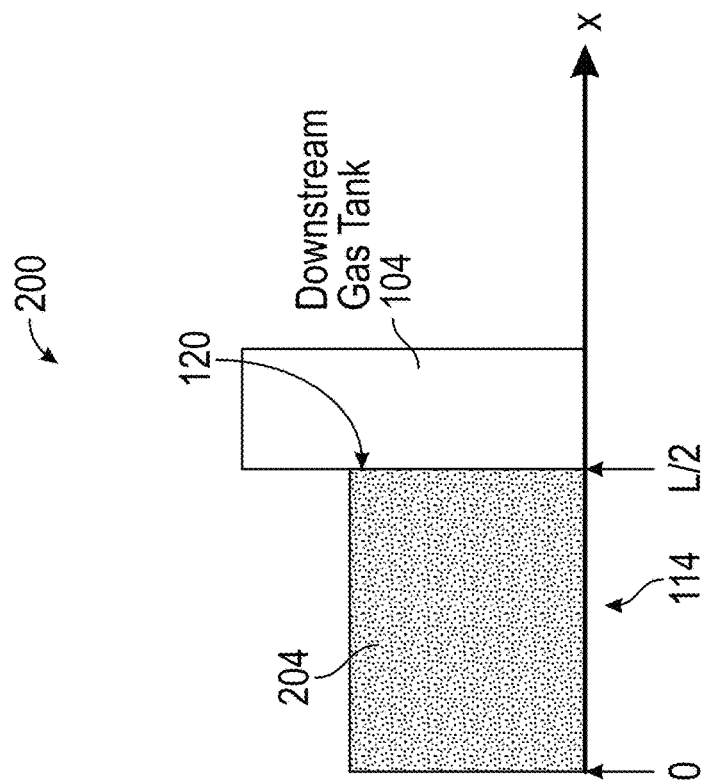
FIG. 2 illustrates the core of FIG. 1, according to a gas flow model.
Figure 2:
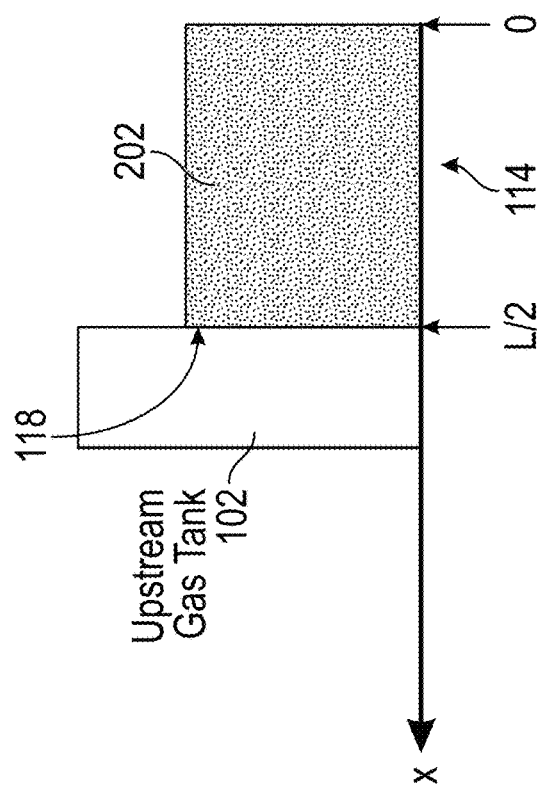

FIG. 2 illustrates the core 114 of FIG. 1, according to a gas flow model 200 (graphical illustration of the gas flow through the core).

For the matrix flow regime (flow structure of the fluid in the core), each half of the core 114 is analyzed independently. An original point is placed in the center of the core 114. The core 114 has a length L and an end cross section area A. The core 114 is divided into a first half 202, which is the upstream half 202, and a second half 204, which is the downstream half 204. A first x-axis shows the location along the first half 202, with the center of the undivided core being the origin of the x-axis and the first end face 118 of the first half 202 being the location L/2 in the x-axis. The first end face 118 at z=L/2 is connected to the upstream gas tank 102. The second half 204 of the core shows a similar construction.

The upstream and downstream halves 202, 204 of the core 114 are in equilibrium with the saturation pressure $P_s$. After the pressure pulses are applied, such that the pressure in the upstream and downstream gas tank 102, 104, as read by the pressure gauges $P_{UT}$, $P_{DT}$, are higher than the pressure inside the core 114, as read by the pressure gauges $P_{UP}$, $P_{DP}$ before the beginning of the measurement, and gas still flows from the upstream gas tank 102 and downstream tank 104 to the core 114 and from the end faces 118, 120 of the core 114. After the beginning of the experiment, the pressure in the upstream pipe 110 is recorded by both pressure gauges $P_{UT}$, $P_{UP}$ and the pressure in the downstream pipe 112 is recorded by the pressure gauges $P_{DT}$, $P_{DP}$.

Only the gas flow from the end faces 118, 120 is considered. In case there is a fracture going parallel to the axis of the cylindrical sample 114 because horizontal sample plugs are used on both sides of the cylindrical sample 114, i.e., the lamination of a sample plug is parallel to the axis of the sample plug, thus the gas flow from the fracture faces to the matrix is negligible due to two reasons: First, a source core from which the cylindrical sample 114 are made is anisotropic and thus the vertical permeability is significantly less than the horizontal permeability. Second, the sample plugs are short such that the area of fracture faces is considerably less than the area of the end faces 118, 120. Therefore, the gas flow into the cylindrical sample 114 in the late stage is mainly from the end faces 118, 120 of the sample plugs. The details of the analytical derivation of the matrix permeability are presented in the following paragraphs.

Matrix Permeability Derivation

In the following description, the matrix permeability $k_{mpfd}$ is calculated using the experimental laboratory system 100 of FIG. 1. Only the analysis of the upstream side of the core 114 is demonstrated below. The analysis for the downstream side is similar. The volume $V_u$ of the upstream gas tank 102 and the volume $V_d$ of the downstream gas tank 104 are chosen based on the pore volume of the core 114. For simplification, it can be chosen that the volume $V_u$ of the upstream gas tank 102 is equal to the volume $V_d$ of the downstream gas tank 104 ($V_d=V_u$). Furthermore, it may be chosen that the pressure on the upstream side $P_u$ is equal to the pressure on the downstream side $P_d$ ($P_d=P_u$) for the sake of simplicity. Consequently, the sum of upstream and downstream volume is transformed to an equivalent volume, $$V_e = V_u + V_u + V_f \tag{1}$$

where $V_f$ is the fracture volume, which is neglectable compared to the volume $V_u$ of the upstream gas tank 102. Thus, the equivalent volume is twice as large as the volume $V_u$ of the upstream gas tank 102 ($V_e = 2 V_u$). Combining Darcy's law and the mass conservation equation, the differential equation P(z, t) for the gas pressure inside the core as a function of the distance z across the sample length along its axis and the elapsed time t is derived as:

$$\frac{\partial^2 P(z,t)}{\partial z^2} = \frac{c\mu\phi_m}{k_{mpfu}} \frac{\partial P(z,t)}{\partial t}, \text{ where } 0 < z < L/2 \tag{2}$$

with the initial conditions:

$$P\left(z = \frac{L}{2}, t = 0\right) = P_u(t=0), \text{ where } z = L/2 \tag{3}$$

$$P(z, t=0) = P_s, \text{ where } 0 < z < L/2 \tag{4}$$

and the boundary conditions:

$$\frac{\partial P(z,t)}{\partial t} = -\frac{k_{mpfu}}{c\mu} \frac{2A}{V_e} \frac{\partial P(z,t)}{\partial z} \text{ where } z = L/2 \tag{5}$$

$$\frac{\partial P(z,t)}{\partial z} = 0, \text{ where } z = 0 \tag{6}$$

Thereby, A is the inlet surface area of the core, P(z, t) is the pressure at location z at the time t at one side of the core with the location 0<z<L/2 or at the contact between the core and the gas tank at the location z=L/2, $P_u(t)$ is the upstream pressure at the time t as recorded by the pressure transducer close to the sample upstream first end face 118 of the core, $P_s$ is the saturation pressure prior to the beginning of the experiment, c is the compressibility, u is the gas viscosity, $k_{pfmu}$ is the matrix permeability (or partially fractured permeability which is a combination of matrix permeability $k_m$ and partial-fracture permeability $k_{pf}$) on the upstream side, and L is the length of the core, and $\phi_m$ is the matrix porosity.

The matrix porosity $\phi_m$ is expressed as:

$$\phi_m = \frac{V_m}{V_b}, \tag{7}$$

where $V_m$ is the matrix pore volume and $V_b$ is the bulk volume of the core. In defining the initial and boundary conditions, we assumed symmetry conditions such that we only focused on one half of the core.

The dimensionless time for the second-stage process τ, is defined as $$\tau = \frac{4k_{mpfu}t}{c\mu\phi_m L^2} \tag{8}$$

and the dimensionless pressure $P_D$ is defined as $$P_D(r, \tau) = \frac{P(z,t) - P_s}{P_u(0) - P_s}, \tag{9}$$

where r is the dimensionless location and τ is the dimensionless time, $P_D(r, \tau)$ is the dimensionless pressure calculated from pressure at the position z and at the time t, $P_s$ is the saturation pressure of the whole system prior to the start of the experiment, and ω1 and r are defined as $$\omega_1 = \frac{V_m}{V_e}, \text{ and} \tag{10}$$

$$r = \frac{2z}{L}. \quad (11)$$

With these dimensionless parameters, Eqs. (6) through (11) are converted to:

$$\frac{\partial^2 P_D(r,\tau)}{\partial r^2} = \frac{\partial P_D(r,\tau)}{\partial \tau}, \text{ where } \tau > 0, 0 < r < 1 \quad (12)$$

$$\omega \frac{\partial P_D(r,\tau)}{\partial r} = -\frac{\partial P_D(r,\tau)}{\partial \tau} \text{ where } \tau > 0, r = 1 \quad (13)$$

$$P_D(r,\tau) = 1, \text{ where } \tau = 0, r = 1 \quad (14)$$

$$P_D(r,\tau) = \frac{P(z,t) - P_s}{P_u(0) - P_s}, \text{ where } \tau = 0, 0 < r < 1 \quad (15)$$

$$\frac{\partial P_D(r,\tau)}{\partial r} = 0, \text{ where } \tau > 0, r = 0 \quad (16)$$

Through the Laplace transform and inverse Laplace transform, the analytical solution for the dimensionless gas pressure of the upstream gas tank ($P_D(r=1, \tau)$ or $P_{Du}(\tau)$) (subscript D stands for dimensionless and u for upstream side) for the matrix flow regime is obtained as:

$$P_{Du}(r=1, \tau) = \frac{P_u(t) - P_s}{P_u(0) - P_s} = \quad (17)$$

$$= 2\sum_{n=1}^{\infty} \exp(-\varphi_{n1}^2 \tau)\left(\frac{1}{\omega + \frac{\varphi_{n1}^2}{\omega} + 1}\right)\left(1 - \frac{1}{\omega + 1}\right)^{-1},$$

where $\varphi_{n1}$ is the n-th solution of the following equation (18), and the subscript 1 indicate the upstream side. The $\varphi_{n1}$ is solved from the following equation $$\tan(\varphi_{n1}) = -\frac{\varphi_{n1}}{\omega_1}, \varphi_{n1} > 0 \quad (18)$$

For practical applications, Eq. (17) is simplified as follows:

$$\log(P_{Du}) = \log\left(\frac{P_u(t) - P_s}{P_u(0) - P_s}\right) \approx \quad (19)$$

$$\approx \log(f_1) - \varphi_{11}^2 \tau = \log(f_1) - \varphi_{11}^2 \frac{4k_{pfmu}}{c\mu\phi_m L^2}t, \text{ with } \varphi_{11} > 0,$$

where $\varphi_{11}$ is the first solution of Eq. (18) for the upstream side, $f_1$ is a constant, $\phi_m$ is the porosity of the matrix which is approximated by the total porosity $\phi_t$, L is the length of the source rock plug sample, and $\varphi_{11}$ is the first non-negative solution of $$\tan(\varphi) = -\frac{\varphi_{n1}}{\omega_1},$$

where $$\omega_1 = \frac{V_m}{V_e}$$

is the ratio of the pore volume of the matrix over the volume of all the connected reservoirs (upstream and downstream reservoirs and the volume of the fractures) when adsorption is neglected. The matrix permeability $k_{mpfu}$ is estimated from the slope, that equals to $$\varphi_{11}^2 \frac{4k_{mpfu}}{c\mu\phi_m L^2},$$

in Eq. (19) by fitting the observed data of $$\log\left(\frac{P_u(t) - P_s}{P_u(0) - P_s}\right)$$

vs. time t, (i.e., $\log(P_{Du})$ vs t). Only the linear curve fitting is needed herein (see FIGS. 5A and 5B, and 7A and 7B).

The solution for the matrix permeability $k_{mpfd}$ for the downstream side is acquired in a similar fashion by replacing $V_u$ with $V_d$, and $P_u$ with $P_d$ $$\log(P_{Dd}) = \log\left(\frac{P_d(t) - P_s}{P_d(0) - P_s}\right) \approx \log(f_2) - \varphi_{12}^2 \tau = \quad (20)$$

$$= \log(f_2) - \varphi_{12}^2 \frac{4k_{mpfd}}{c\mu\phi_m L^2}t, \varphi_{12} > 0$$

Figure 3:
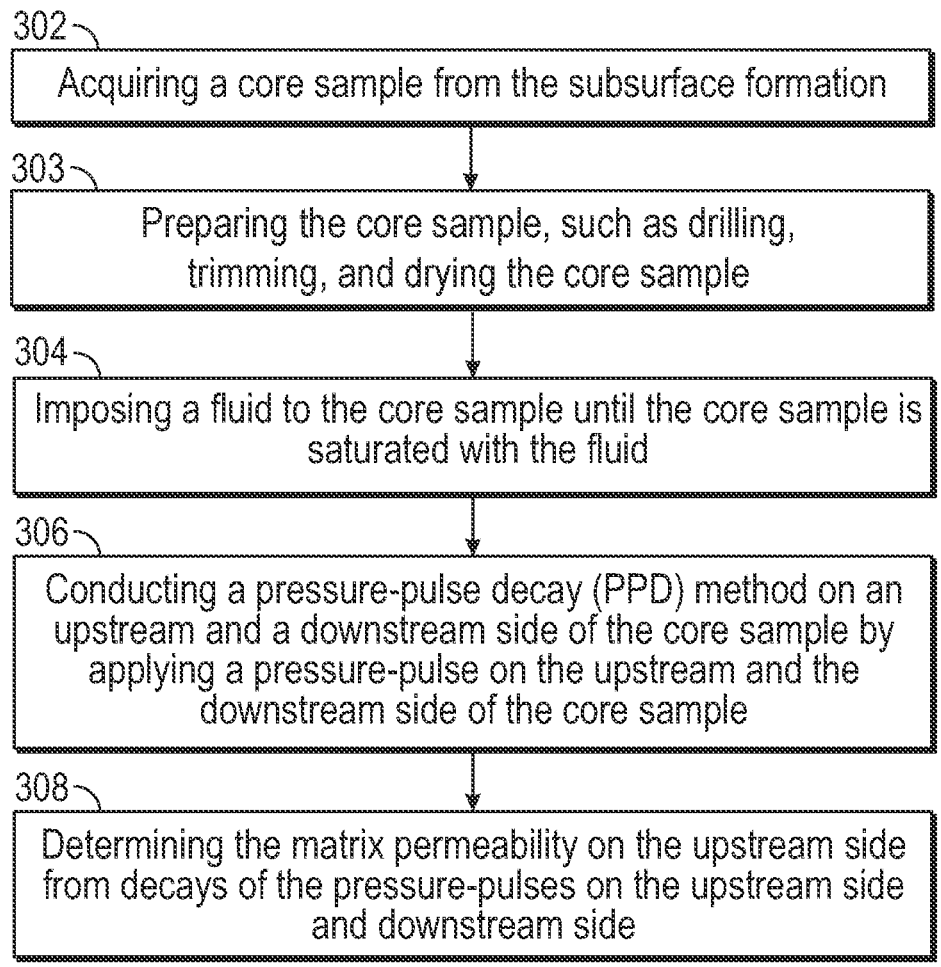
FIG. 3 shows a flowchart of the method steps for determining a matrix permeability of a subsurface formation, according to one or more embodiments.

FIG. 3 shows a flowchart of the method steps for determining a matrix permeability of a subsurface formation. The method steps are the following.

In step 302, a core is acquired from the subsurface formation.

In step 303, the core sample is prepared. The preparing of the plug sample includes drilling, trimming, and drying the plug sample.

In step 304, a fluid is imposed to the core until the core is saturated with the fluid. In one or more embodiments, the fluid is liquid. In other embodiments, the fluid is a gas, such as a noble gas, like nitrogen $N_2$.

In step 306, a pressure-pulse decay (PDP) method is conducted on an upstream and a downstream side of the core by applying a pressure-pulse on the upstream and the downstream side of the core. The two pressure-pulses are applied on the upstream and downstream sides of the core simultaneously.

A source-rock core sample may have a plethora of fractures and microfractures due to its lamination nature. During the PDP method, the fluid flow in a fracture or microfracture is much faster than that in the pure matrix because a fracture or microfracture has much higher permeability values than those for the rock matrix. It is not uncommon for a fracture or microfracture to cut into one side of the rock sample and die out in the middle of the rock sample, causing the permeability values on both end of the sample largely different from each other. Thus, the method disclosed herein addresses the sample with fractures appearing on one end and not present on the other.

In step 308, the matrix permeability on the upstream side is determined from decays of the pressure-pulses on the upstream side and downstream side, respectively. The matrix permeability on the upstream side is determined using the following equation:

$$\log(P_{Du}) \approx \log(f_1) - \varphi_{11}^2 \frac{4k_{mpfu}}{c\mu\phi_m L^2} t$$

(see Eq. (19)). The matrix permeability on the downstream side is determined using the following equation:

$$\log(P_{Dd}) \approx \log(f_2) - \varphi_{12}^2 \frac{4k_{mpfd}}{c\mu\phi_m L^2} t$$

(see Eq. (20)).

Figure 4:
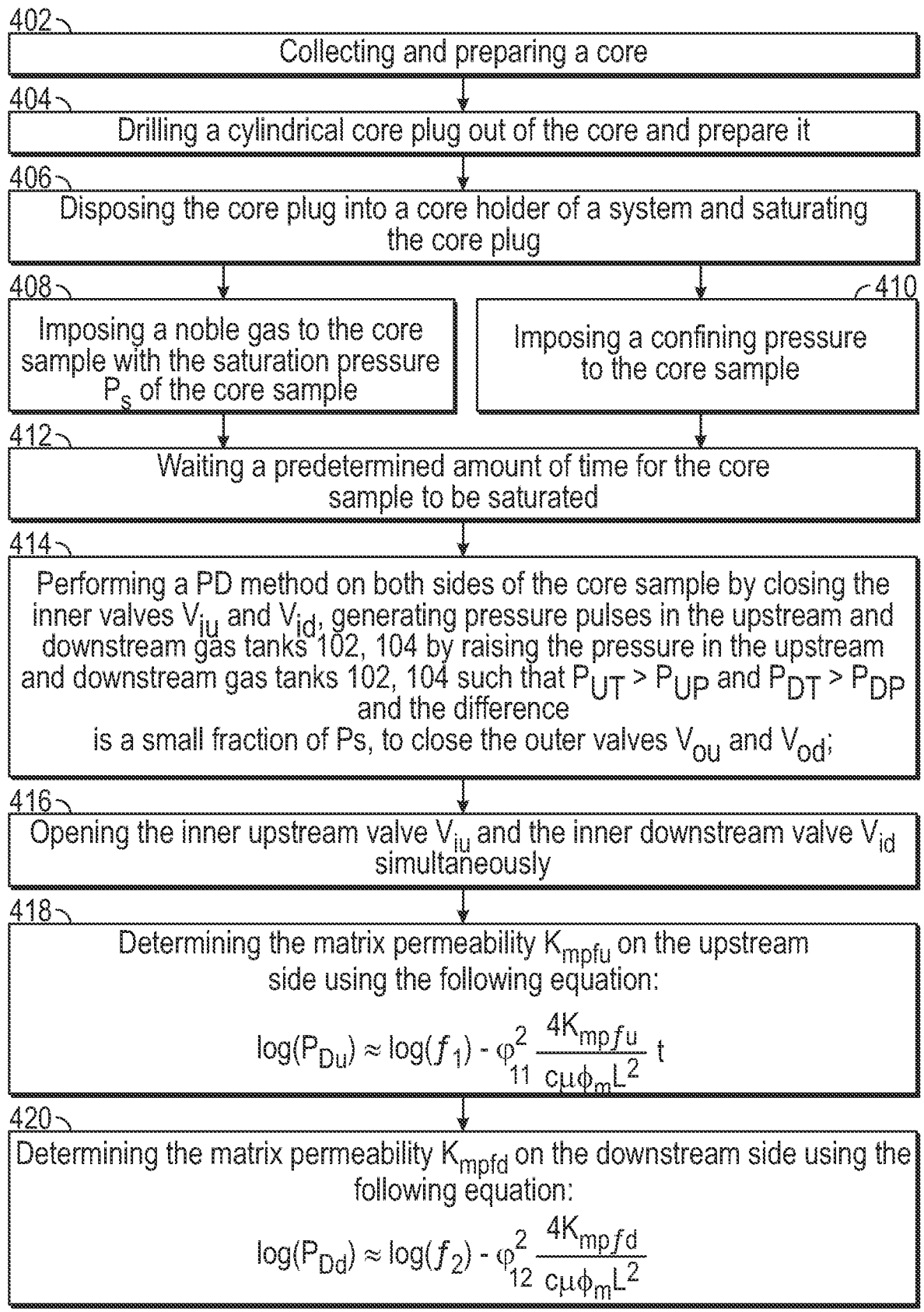
FIG. 4 shows a flowchart of the method steps for determining a matrix permeability of a subsurface formation, according to one or more embodiments.

FIG. 4 shows a flowchart of the method steps for determining a matrix permeability of a subsurface formation. The following method steps may be performed using the system 100 of FIG. 1.

In step 402, a core is collected and prepared. In one or more embodiments, the core is collected from an unconventional reservoir.

In step 404, a cylindrical core plug is drilled out of the core and prepared. In one or more embodiments, the core plug has a diameter of 1 to 1.5 inches and has a length of 1 to 2 inches. Furthermore, mobile water and hydrocarbon fluids are removed from the core plug.

It is generally assumed that the core plug of a source core is homogeneous along its axis and a fracture, if present, goes through the whole sample, which is a reasonable approximation and accurate for most source cores. However, a small number of cores contain fractures which don't go through all the sample length. The cores create a situation that at one end the fracture(s) is/are present and at another end of the core there are no fractures. In this case the matrix permeability varies from the first end face 118 to the second end face 120, with the end that a fracture or fractures reside having a larger matrix permeability reflecting the presence of fractures. The lower permeability from the other end is more representative of the matrix permeability of the source core.

In step 406, the core plug is disposed into the core holder 106 of the system 100. The core holder must have no leakage from all its connections, the pore lines, and the connections to the sample and to the pump(s) must have no leakage either to the surrounding atmosphere or from the confining fluid, and the temperature of the oven needs to be stabilized.

Steps 408 and 410 may be carried out concurrently or in sequence, with step 410 followed by step 408. In either case, the confining pressure must be higher than the pore pressure at any time. In step 408, gas is imposed to the core with the saturation pressure $P_s$ of the core, e.g., 2,500 psi. The use of the saturation pressure $P_s$=2,500 psi is to minimize the impact of diffusion on the matrix permeability.

For imposing the noble gas, the first pump 116 and the second pump 108 can be used. The inner upstream valve $V_{iu}$, the outer upstream valve $V_{ou}$, the inner downstream valve $V_{id}$, and the outer downstream valve $V_{od}$ are opened, and the core is saturated with a predetermined pressure, e.g., 2500 psi. The predetermined pressure of 2500 psi is selected because at this pressure and an experimental temperature (e.g., 50° C.) the flowing gas, e.g., $N_2$, stays in supercritical state (occurs for a gas at a specific temperature and pressure such that the gas will no longer condense to a liquid regardless of how high the pressure is raised). Thus, the gas slippage effect (a phenomenon that will occur when gas flowing through fractures of the core, controls gas flow behavior and severely affects the ability of gas flow in tight sandstone gas reservoir) is minimal and is neglected during the data analysis.

In step 410, a confining pressure 132 is imposed to the core by a confining pressure pump 126. The confining pressure 132 is at least 500 psi higher than the gas pressure used anytime including in step 408. The use of the confining pressure 132 is to ensure proper sealing of the core. Step 410 is performed parallel to step 408, or before step 408.

In step 412, a waiting a predetermined amount of time for the core to be saturated. In one or more embodiments, the predetermined waiting time is eight to sixteen hours. In other embodiments, the predetermined waiting time is eight to twenty-four hours. This is because it takes time for the rock to equilibrate with different pore pressures and confining pressures.

After the predetermined waiting time, when the core is saturated, the inner upstream valve $V_{iu}$ and the inner downstream valve $V_{id}$ are closed and the pressure in the upstream and downstream gas tanks 102, 104 are raised slightly higher than the saturation pressure (e.g., 2500 psi) of the core by the first pump 116 and second pump 108. Then the outer upstream valve $V_{ou}$ and the outer downstream valve $V_{od}$ are closed to isolate the upstream and downstream gas tanks 102, 104 respectively. The pressure is chosen such that the pressure difference is small enough for the resulting changes in fluid density and viscosity to be neglected.

In step 414, the PDP method is performed on both sides of the core by closing the inner valves $V_{iu}$ and $V_{id}$, generating pressure pulses in the upstream and downstream gas tanks 102, 104 by raising the pressure in the upstream and downstream gas tanks 102, 104 such that $P_{UT}>P_{UP}$ and $P_{DT}>P_{DP}$ (e.g., 2600) and the difference is a small fraction of $P_s$, to close the outer valves $V_{ou}$ and $V_{od}$. The slight pressure difference is a fraction of the saturation pressure, e.g., 2500 psi. After the gas fills the dead volumes, the initial gas pressure is significantly less than the tank pressure of 2600 psi. Thus, the change in gas density and viscosity of the core is neglectable.

A short time of a few minutes is needed for stabilizing the pressures in the upstream and downstream gas tanks 102, 104 and the inner upstream valve $V_{iu}$ and the inner downstream valve $V_{id}$ are opened in step 416 to begin the $P_{DP}$ methods as in step 416. The pressures are automatically recorded at a small time-interval, (e.g., every 7 ms). The $P_{DP}$ methods end when the pressure in the system 100 doesn't change.

In step 416, the inner upstream valve $V_{iu}$ and the inner downstream valve $V_{id}$ are opened simultaneously. This step is performed by an acquisition software with a button to click on. The pressure data is recorded automatically.

In step 418, the matrix permeability $k_{mpfu}$ on the upstream side is determined on the upstream side using the following equation:

$$\log(P_{Du}) \approx \log(f_1) - \varphi_{11}^2 \frac{4k_{mpfu}}{c\mu\phi_m L^2} t$$

In step 420, the matrix permeability $k_{mpfd}$ on the downstream side is determined on the downstream side using the following equation:

$$\log(P_{Dd}) \approx \log(f_2) - \varphi_{12}^2 \frac{4k_{mpfd}}{c\mu\phi_m L^2} t$$

Figure 5A:
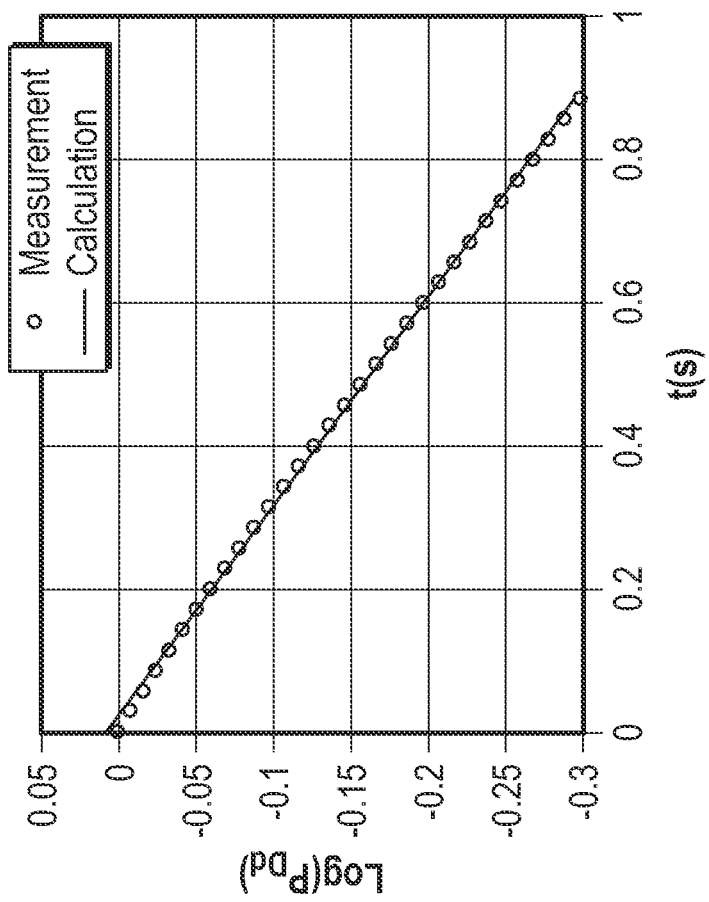
FIG. 5A shows a measured and a calculated plot of the logarithm of the gas pressure in the upstream gas tank as function of the elapsed time, for a first core, according to one or more embodiments.

FIG. 5A shows a measured and a calculated plot of the logarithm of the gas pressure $P_{Du}$ in the upstream gas tank 102 (see FIG. 1) as function of the elapsed time t, for a first core example (or sample). The calculated plot is based on the analytical solution of Eq. (19). In one or more embodiments, the core sample is a pyrophyllite core that is not fractured. In other embodiments, the core sample is a homogeneous and light metamorphic core.

The measurement of the matrix permeability is performed simultaneously with the decay of the pressure-pulse from upstream and downstream sides to demonstrate the validity of the simultaneous PD method. Both, the measured and the calculated plots show a conform linear relationship between the logarithm of the gas pressure $P_{Du}$ and the elapsed time t.

In the conventional pressure pulse decay test (PD), the pulse is only introduced from the upstream of the core. Performing the conventional PD on the second core results in a matrix permeability of 202 nD. The results of the data analysis, using the PD method on the upstream and downstream side simultaneously, show that the matrix permeability at the upstream side is $k_{mu}$=204 nD and at the downstream side is $k_{md}$=197 nD. These values are very close to each other and are also in a good agreement with the value obtained from the PD method performed on the upstream and downstream side separately, indicating that the latter method, accurately measures the permeability of a core.

Figure 5B:
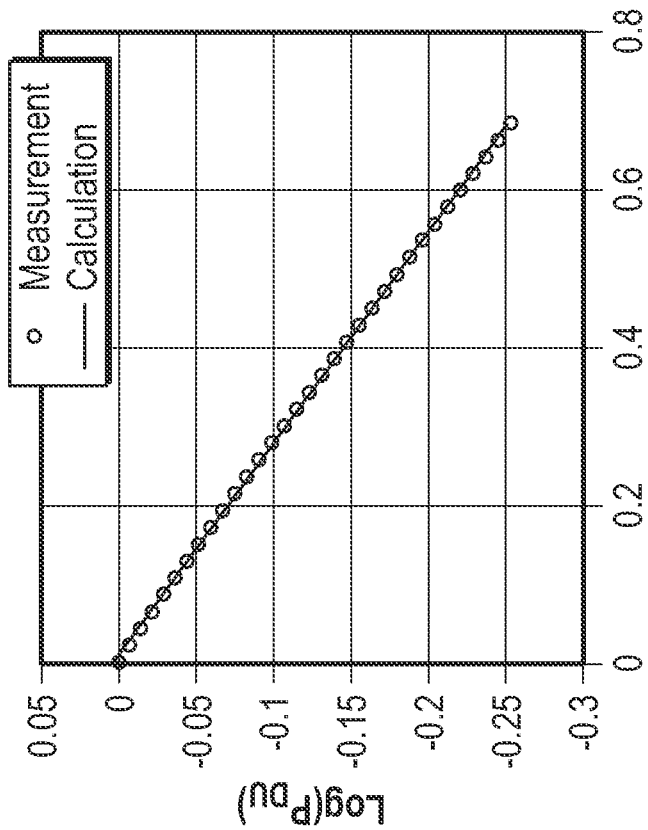
FIG. 5B shows a measured and a calculated plot of the logarithm of the gas pressure in the downstream gas tank as function of the elapsed time, for the first core, according to one or more embodiments.

FIG. 5B shows a measured and a calculated plot of the logarithm of the gas pressure $P_{Dd}$ in the downstream gas tank 104 (see FIG. 1) as function of the elapsed time t, for the first core. The calculated plot is based on the analytical solution of Eq. (20). Both, the measured and calculated plot show a conform linear relationship between the logarithm of the gas pressure $P_{Dd}$ and the elapsed time t.

Figure 6:
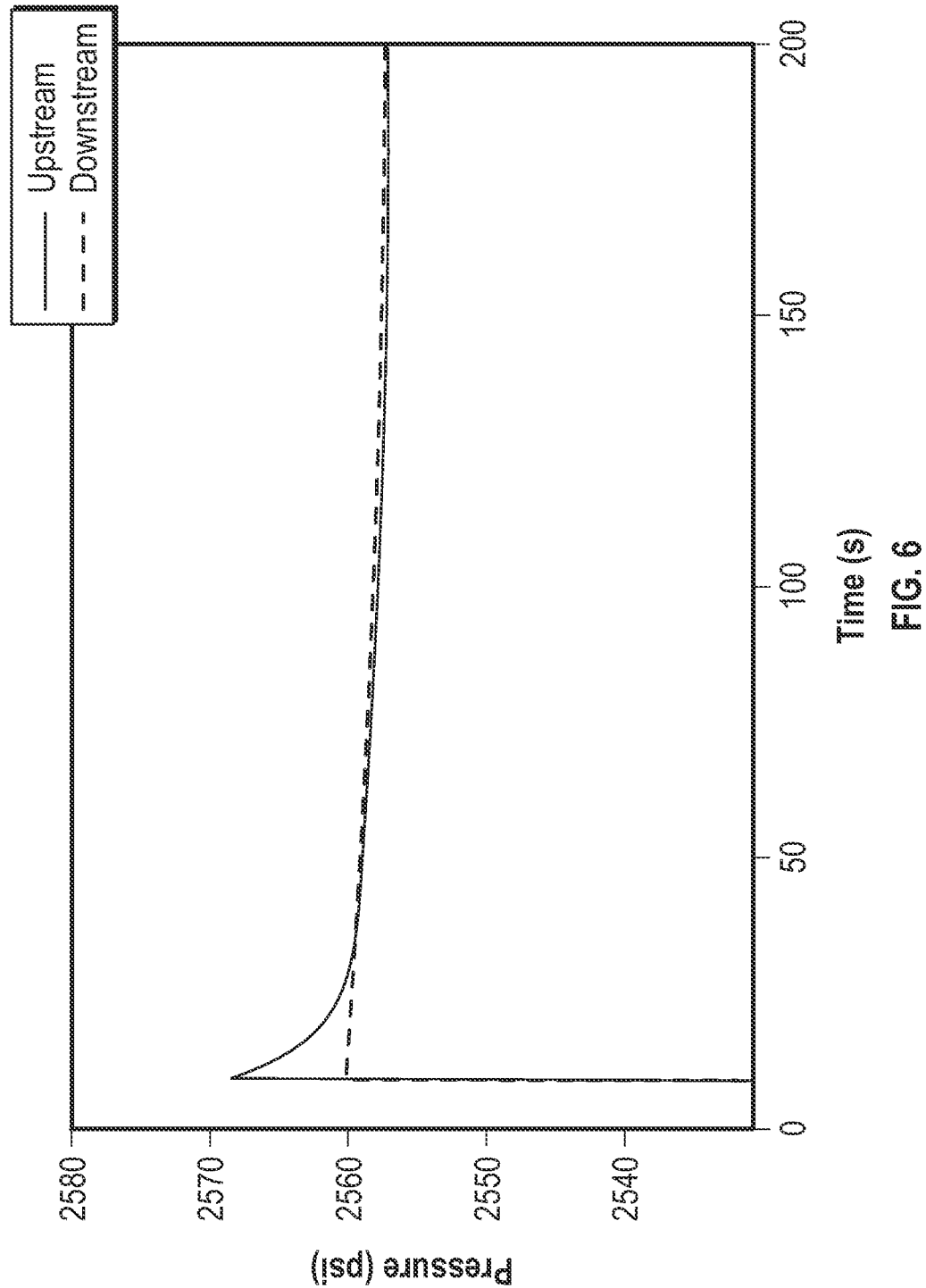
FIG. 6 shows a plot of the pressure on the upstream side and a plot of the pressure on the downstream side, for the second core, according to one or more embodiments.

FIG. 6 shows a plot of the pressure on the upstream side (solid line) and a plot of the pressure on the downstream side (dashed line), for the second core sample. Both plots are plotted as function of the elapsed time t. The pressures are recorded by the transducers near the second core. At the time t=0 s the pressure at the upstream side shows a peak that indicates the opening of the inner upstream valve $V_{iu}$ and the inner downstream valve $V_{id}$ for the PD method.

The second sample is a carbonate source core and shows visibly the presence of microfracture on the upstream side of the second core and the lack of fracture on the other end. The plot demonstrates that the matrix permeability is accurately measured even when the core is partially fractured.

Figure 7B:
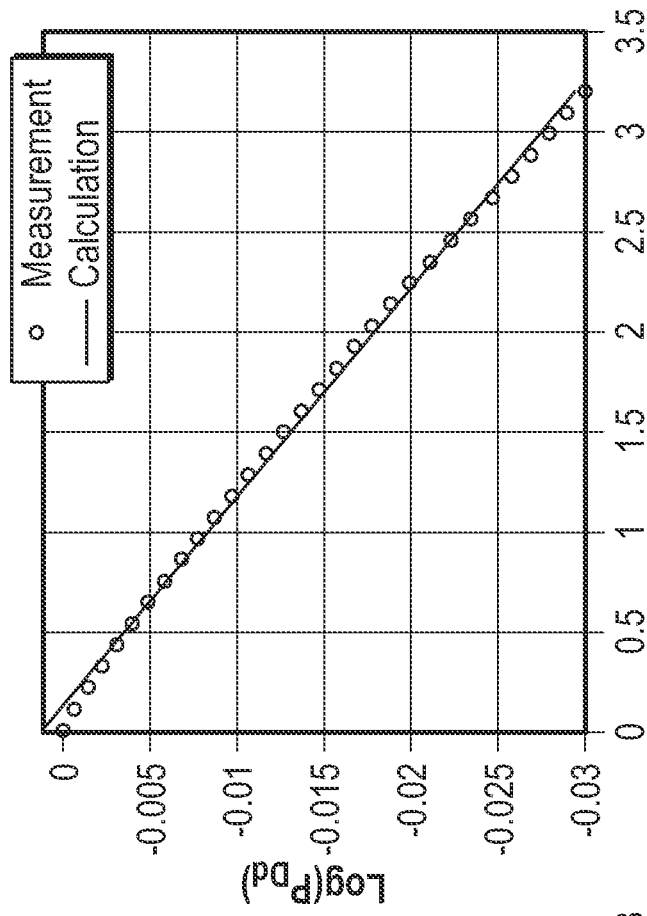
FIG. 7B shows a measured and a calculated plot of the logarithm of the gas pressure in the downstream gas tank as function of the elapsed time, for the second core, according to one or more embodiments.
Figure 7A:
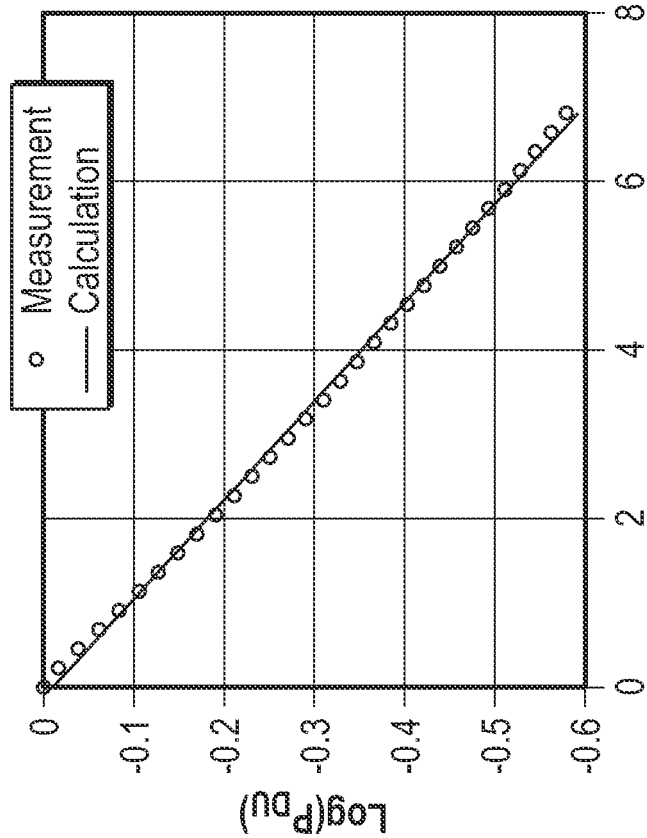
FIG. 7A shows a measured and a calculated plot of the logarithm of the gas pressure in the upstream gas tank as function of the elapsed time, for the second core, according to one or more embodiments.

FIG. 7A shows a measured and a calculated plot of the logarithm of the gas pressure $P_{Du}$ in the upstream gas tank 102 (see FIG. 1) as function of the elapsed time t, for the second core. The calculated plot is based on the analytical solution of Eq. (19). Both, the measured and calculated plots show a conform linear relationship between the logarithm of the gas pressure $P_{Du}$ and the elapsed time t.

FIG. 7B shows a measured and a calculated plot of the logarithm of the gas pressure $P_{Dd}$ in the downstream gas tank 104 (see FIG. 1) as function of the elapsed time t, for the second core. The calculated plot is based on the analytical solution of Eq. (20). Both, the measured and calculated plot show a conform linear relationship between the logarithm of the gas pressure $P_{Dd}$ and the elapsed time t.

FIGS. 7A and 7B show a graphic solution of the values for the upstream and downstream matrix permeability of the source core resolved from the linear relationship between the logarithm of the dimensionless $P_{Du}/P_{Dd}$ and time. As mentioned before, the matrix permeability (partial-fracture permeability) on each side is extracted graphically by plotting the log ($P_{Du}$) or log($P_{Dd}$). The results of the data analysis show that the combined partial-fracture permeability and the matrix permeability on the upstream side is $k_{pf}$=109 nD and the matrix permeability on the downstream side is $k_m$=12 nD. Thus, the representative matrix permeability is 12 nD for the second core. It should be emphasized that $k_{pf}$ is the combination of matrix permeability (related to flow through rock matrix from the upstream reservoir) and partial-fracture permeability (related to the flow into the fracture) is much smaller than the fracture permeability because the fracture penetration into the sample is short. The fracture permeability for fractures that connect the two ends of the sample is on the order of 1000 nD.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for determining a matrix permeability of a subsurface formation, comprising the steps:
   acquiring a core from the subsurface formation,
   imposing a fluid to the core until the core is saturated with the fluid,
   conducting a pressure-pulse decay (PD) method on an upstream and a downstream side of the core by applying a pressure-pulse on the upstream and the downstream side of the core, and
   determining the matrix permeability from decays of the pressure-pulses on the upstream side and downstream side.

2. The method of claim 1, further comprising applying a confining pressure to the core to ensure proper sealing of the core.

3. The method of claim 2, wherein the confining pressure is higher than the pressure of the fluid at any time.

4. The method of claim 2, wherein the confining pressure is applied before the PD method.

5. The method of claim 2, wherein the confining pressure is performed by a confining pressure pump.

6. The method of claim 2, wherein a pore pressure of the fluid is smaller than the confining pressure.

7. The method of claim 2, further comprising stopping the confining pressure after the PD method.

8. The method of claim 2, wherein the confining pressure is constant.

9. The method of claim 1, wherein the pressure-pulse is a fraction of the saturation pressure of the core.

10. The method of claim 1, wherein the fluid is a liquid.

11. The method of claim 1, wherein the fluid is a gas.

12. The method of claim 11, wherein the gas comprises a noble gas.

13. The method of claim 11, wherein the gas comprises nitrogen.

14. The method of claim 11, wherein the gas is pressured.

15. The method of claim 11, wherein the gas is imposed with the saturation pressure of the core.

16. The method of claim 1, wherein the core is saturated in eight to sixteen hours.

17. The method of claim 1, wherein the core is saturated in eight to twenty four hours.

18. The method of claim 1, wherein the pressure-pulse on the upstream and downstream side is applied on the core simultaneously.

19. The method of claim 1, wherein the matrix permeability on the upstream side is determined using the following equation:

$$\log(P_{Du}) \approx \log(f_1) - \varphi_{11}^2 \frac{4k_{mpfu}}{c\mu\phi_m L^2} t.$$

20. The method of claim 1, wherein the matrix permeability on the downstream side is determined using the following equation:

$$\log(P_{Dd}) \approx \log(f_2) - \varphi_{12}^2 \frac{4k_{mpfd}}{c\mu\phi_m L^2} t.$$

* * * * *